United States Patent [19]
Jinotti

[11] Patent Number: 5,511,545
[45] Date of Patent: Apr. 30, 1996

[54] VALVE FOR PULMONARY MEDICAL USE

[76] Inventor: Walter J. Jinotti, 10 Scott St., New Brunswick, N.J. 08903

[21] Appl. No.: 368,361

[22] Filed: Jan. 4, 1995

[51] Int. Cl.⁶ ............................................. A61M 16/00
[52] U.S. Cl. ............................. 128/205.24; 128/207.14; 128/207.16
[58] Field of Search ........... 128/205.24, 207.14–207.17, 128/205.19, 200.24, 911, 912; 221/27, 154, 303, 312 C; 206/528, 536; 220/4.01–4.07, 720, 724–727, DIG. 12, DIG. 14; 604/181, 905

[56] References Cited

U.S. PATENT DOCUMENTS

| | | | |
|---|---|---|---|
| 2,404,020 | 7/1946 | Akerman | 128/202.11 |
| 3,902,877 | 9/1975 | Swaim | 55/490 |
| 4,291,691 | 9/1981 | Cabal et al. | 128/204.18 |
| 4,595,005 | 7/1986 | Jinotti | 128/205.24 |
| 4,915,132 | 4/1990 | Hodge et al. | 128/205.24 X |
| 5,088,486 | 2/1992 | Jinotti | 128/207.14 |
| 5,140,983 | 8/1992 | Jinotti | 128/207.14 |
| 5,255,672 | 10/1993 | Jinotti | 128/200.26 |

FOREIGN PATENT DOCUMENTS

| | | | |
|---|---|---|---|
| 0347026 | 12/1989 | European Pat. Off. | 128/205.24 |
| 2915683A1 | 10/1979 | Germany | 128/205.24 |

*Primary Examiner*—Edgar S. Burr
*Assistant Examiner*—Eric P. Raciti
*Attorney, Agent, or Firm*—Robert A. Green

[57] ABSTRACT

A valve for pulmonary medical use includes first and second valve portions which are coupled together so that they can rotate with respect to each other and feed oxygen or suction to a patient. The two portions are held together by locking means made up of male and female portions which engage each other in such a way as to pull the two portions of the valve toward each other to hold them in tight coupling.

19 Claims, 6 Drawing Sheets

VALVE FOR PULMONARY MEDICAL USE

BACKGROUND OF THE INVENTION

The present inventor has devised a number of pulmonary dual-purpose catheters which can be used to provide suction and oxygen and medication to a pulmonary patient. These catheters use a valve for controlling the flow of oxygen or suction or medication to a patient and this valve is described and claimed in U.S. Pat. Nos. 4,595,005 5,088,486 which are incorporated herein by reference.

These valves operate perfectly satisfactorily. However, some of their structural features are not amenable to mass production. These valves comprise two portions which are held together securely and are rotatable with respect to each other to control the flow of suction or oxygen to a patient.

SUMMARY OF THE INVENTION

The present invention provides a two way suction-oxygen flow control valve including two portions which are coupled together in a novel manner which provides tight coupling between the parts.

DESCRIPTION OF THE INVENTION

Figure 1:
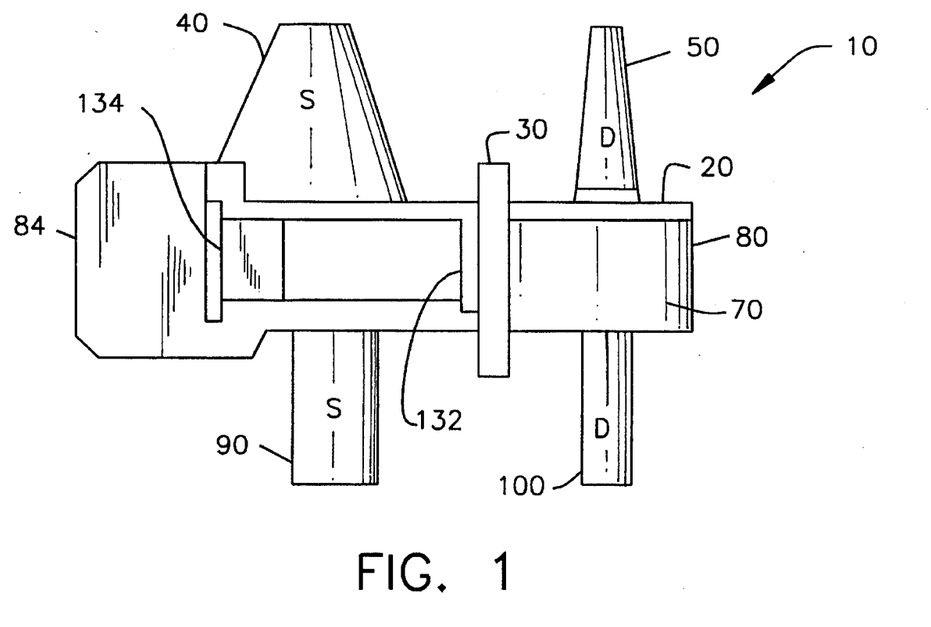
FIG. 1 is a side elevational view of a valve embodying the invention.
Figure 2:
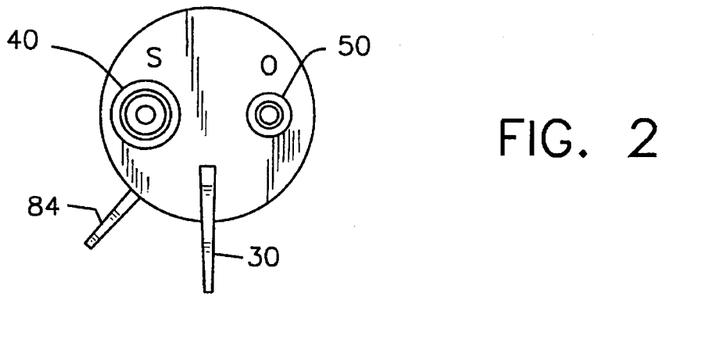
FIG. 2 is a top plan view of the valve of FIG. 1.
Figure 3:
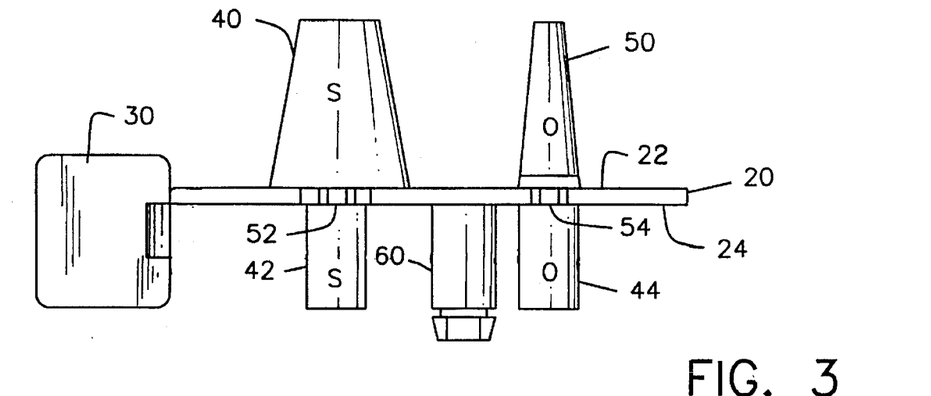
FIG. 3 is a side elevational view of a portion of the valve of FIG. 1.

Referring to FIG. 1, a valve 10 embodying the invention, which is molded of a suitable plastic, has a first portion or supply portion 20 which includes a thin flat circular disk 21 (FIG. 2) The disk 21 has a flat top surface 22 and a flat bottom surface 24. A relatively large-area finger tab 30 is secured to the periphery of the first portion 20. Two tubes 40 and 50 extend from the top surface 22 of the disk 21 (FIGS. 1 and 2) and they communicate with the inside of the first valve portion 20 through holes 52 and 54 in the disk.

The tube 40 is operated as a suction tube and, in an operating system, is connected to a source of suction (not shown) and tube 50 is operated as an oxygen tube which is similarly connected to a source of oxygen (not shown). The tubes 40 and 50 communicate through holes 52 and 54 in the disk 20 with the inside of the valve 10 and with tubes 42 and 44 which extend downwardly from the lower surface 24 of the first portion disk 20. The tubes 42 and 44 are suction and oxygen tubes, respectively, and they are the same length and their lower ends are as smooth as possible.

Figure 4:
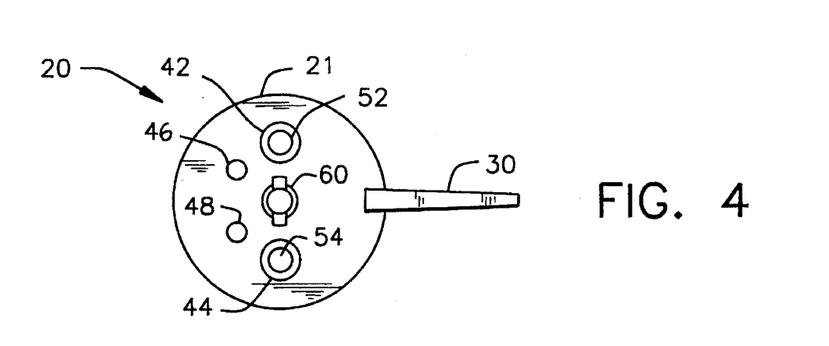
FIG. 4 is a bottom view of a portion of the valve of FIG. 1.
Figure 5:
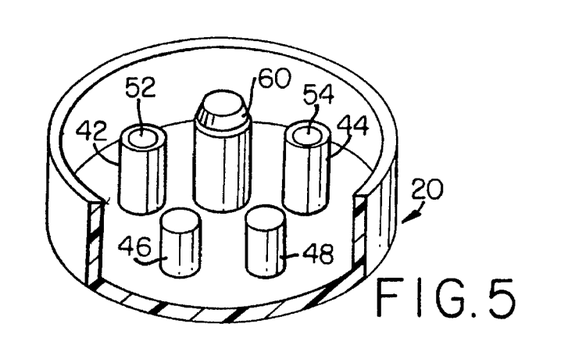
FIG. 5 is a perspective view of the part shown in FIG. 3.

Two solid blocking posts 46 and 48 (FIGS. 4 and 5) also extend downwardly from the lower surface of disk 21 and suitably positioned for a purpose to be described. The blocking posts 46 and 48 are of the same length as tubes 42 and 44 and their lower ends are made as smooth as possible.

A locking and coupling post 60 extends vertically downwardly from the lower surface 24 of disk 21 at about the center therof. The post 60 is shown in greater detail in FIG. 10.

The valve 10 includes a second portion or output portion or patient portion 70 (FIG. 6) which is also molded of plastic, is generally circular in form and is cup shaped. The second portion 70 includes a flat bottom wall 72 having a flat outer surface 74 and a flat, smooth inner surface 76 and a circumferntial wall 80. The inner surface 76 is as smooth as possible, as if it were optically ground, for a purpose to be described. A finger tab 84 is secured to, or formed integrally with, the circumferential wall 80.

A suction tube 90 and an oxygen tube 100 are secured to or formed integrally with the bottom surface 74 of the bottom wall 72. The tubes 90 and 100 communicate through holes 92 and 96, respectively, in the bottom wall with the inside of the second portion 70 and with the tubes 42 and 44, separately, when the valve 10 is assembled and operated as described below. The tubes 90 and 100 are output tubes which are coupled to a patient by means of apparatus to be described below.

Figure 7:
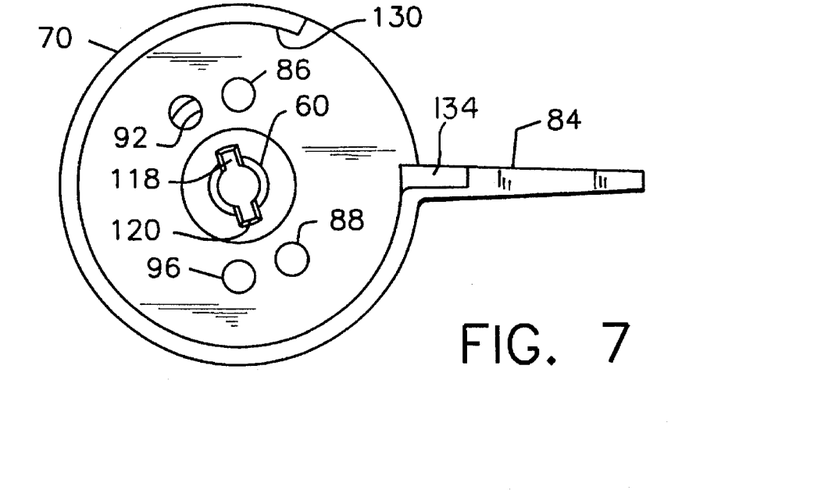
FIG. 7 is a plan view looking into the part shown in FIG. 6.
Figure 8:
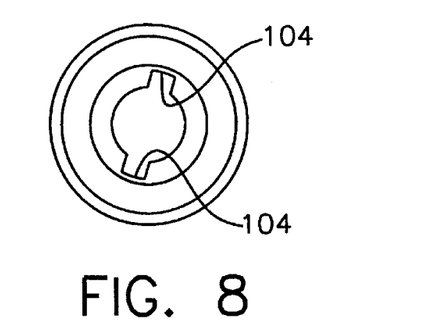
FIG. 8 is a plan view of a portion of the part shown in FIG. 6.
Figure 9:
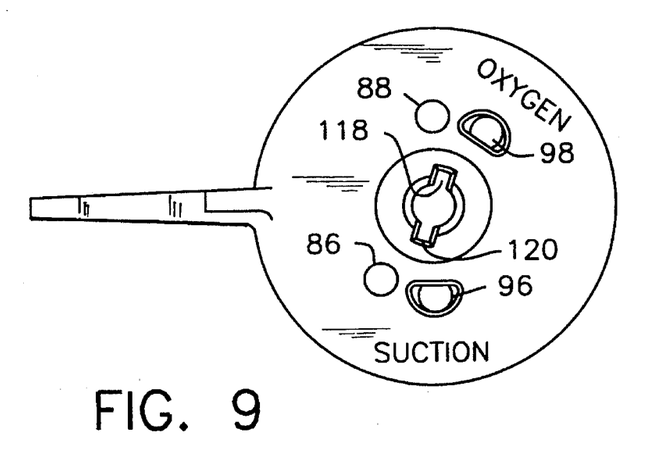
FIG. 9 is a bottom plan view of the valve of FIG. 1.

Two vent holes 86 and 88 are provided in the bottom wall of the second valve portion (FIG. 7 and 9).

A locking tube 102 (FIGS. 6 and 10) is provided on the top surface 76 of bottom wall 72. The tube 102 locks with post 60, and is in the form of a funnel which decreases in diameter from top to bottom. The locking tube 102 is positioned at the center of the second valve portion 70 so that it is aligned with the locking post 60 and can be secured thereto.

Figure 6:
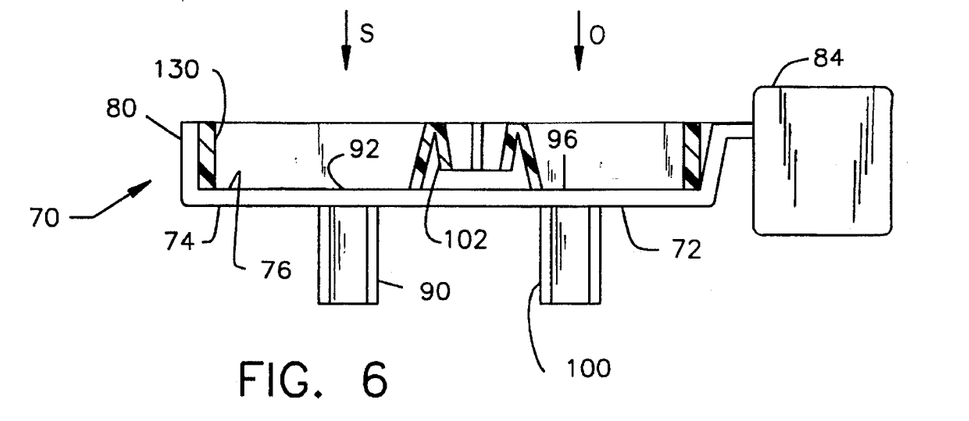
FIG. 6 is a side elevational view of another portion of the valve of FIG. 1.
Figure 10:
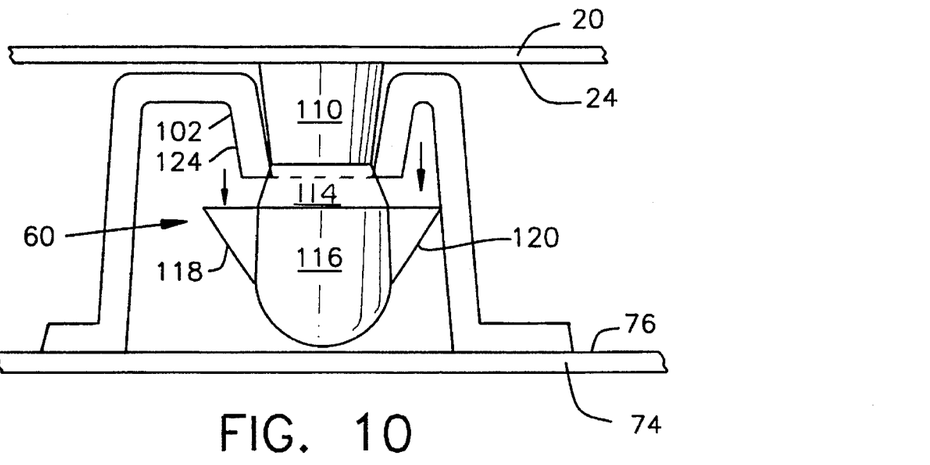
FIG. 10 is an enlarged view of a portion of the valve of the invention.

The wall of locking tube 102 can flex and it includes grooves 104 in its inner surface and spaced apart along the wall. The grooves extend from top to bottom of tube 102.

Referring to FIG. 9 for a detailed description of the locking mechanism of the invention, the post 60 includes a first portion 110 which is generally tubular but is shaped like a truncated cone which decreases in diameter from top to bottom. At the lower end of the portion 110 is a second tubular portion 114 which is also like a truncated cone which increases in diameter from top to bottom and this portion terminates in a tip 116 having two diamterically opposed protruding tab portions 118 and 120.

When the post 60 is inserted into the tapered tube 102, the wall of the tube, which is flexible is biased toward and bears against the first portion 110 and the upper end of the wall, which has slots 104 formed therein, and the portion 114 presses into the slots. The wall of the tube 102 is urged toward the post 60 and pulls the post down and thereby pulls the first portion of the valve toward the second portion to form a very tight, leakproof, fit between the parts.

Figure 11:
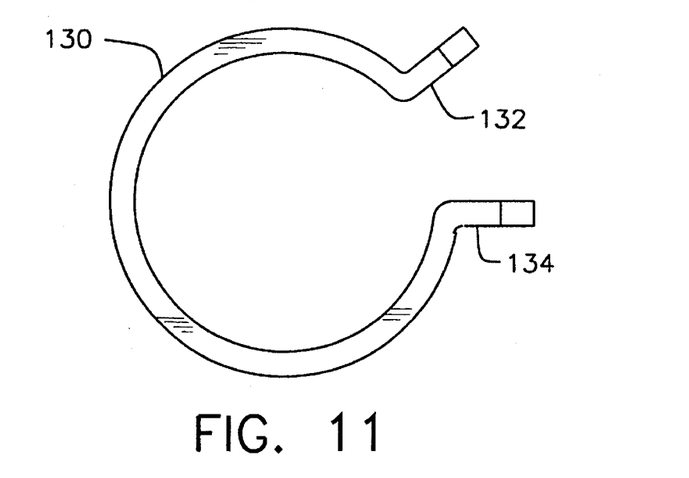
FIG. 11 is a plan view of a spring used in the valve of FIG. 1 in one mode of its operation.
Figure 12:
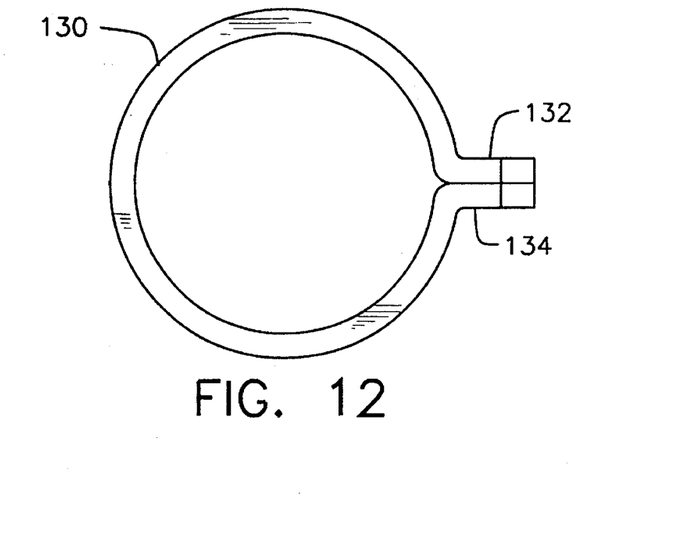
FIG. 12 is a plan view of the spring of FIG. 1 in another mode of its operation.

A plastic spring 130 shown in FIGS. 1, 6, 1 and 12 is seated in the second valve portion 70, in the cup formed thereby and bearing against the inside surface of the wall 80. The spring has one end 132 formed as a tab which bears against one finger tab 30 and the other end similarly formed as a tab 134 which bears against the other finger tab 84.

The valve 10 operates as follows. In the open position of the finger tabs, the spring 130 is open as shown in FIG. 11 and urges the tabs away from each other. In this orientation of the valve parts, the oxygen supply feeds oxygen to tube 50 which is aligned through the valve 10 with the hole 54, tube 44, hole 96 and output tube 100 to a patient. At this time, the suction supply which is on draws air into the vent hole 86 and prevents suction from being applied to the patient. At the same time, the blocking post 46 covers the hole 92 and seals off the outlet suction tube 90 and prevents suction from being applied to the patient. The smooth end of the blocking post 46 and the smooth surface of bottom wall 72 insure a gas-tight fit between the parts.

When the finger tabs are closed and the spring is compressed as shown in FIG. 11, the blocking post 46 is removed from its position blocking hole 92 and input suction tube 40 is coupled through tube 52 and hole 92 to the output suction tube 90 and suction is applied to the patient. At the same time, the other blocking post 48 blocks the oxygen output path in a tight fit as described above and oxygen which is flowing from the supply flows out of the vent hole 88.

The valve of the invention has many advantages due primarily to the fact that the valve has an extremely tight construction, that is its two parts are secured together in a very tight fit. One of the resultant advantages is that suction operates very efficiently. In addition, liquids can be injected into the valve through the oxygen tube 50 under pressure.

Figure 13:
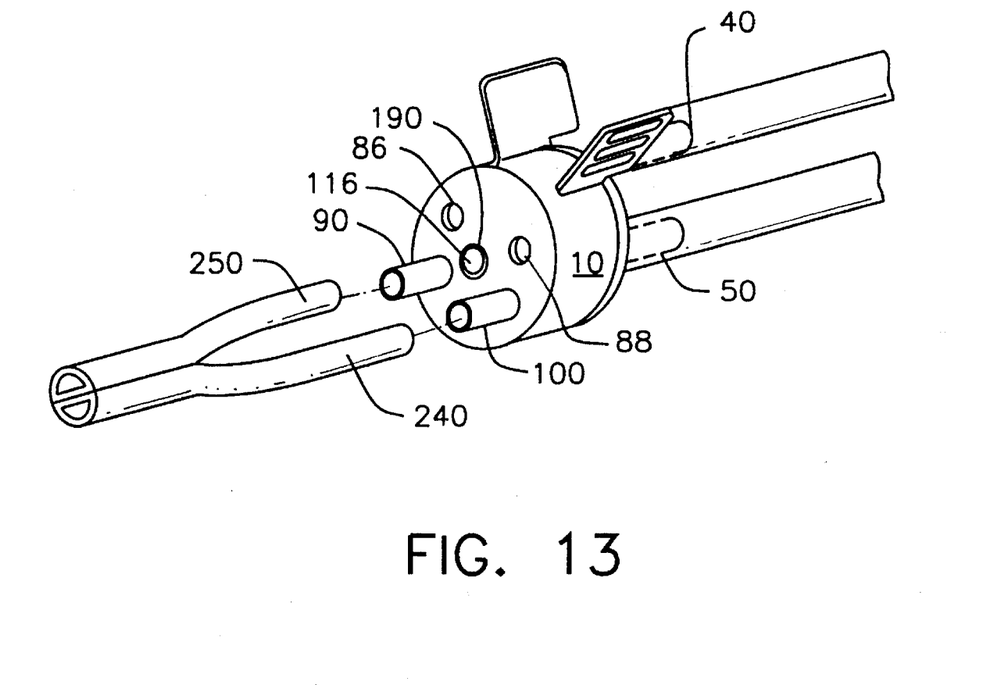
FIG. 13 is perpective view of a system in which the valve of the invention is used.

The valve 10 can be used in a large number of operating systems. One system is shown in U.S. Pat. No. 4,595,005 of Walter J. Jinotti which is incorporated herein by reference. In such a system shown in FIG. 13, the oxygen and suction supplies are connected by suitable tubing to the tubes 40 and 50 of the valve 10 and the output tubes 90 and 100 are connected to flexible tubes 240 and 250 which lead to the patient.

Figure 14:
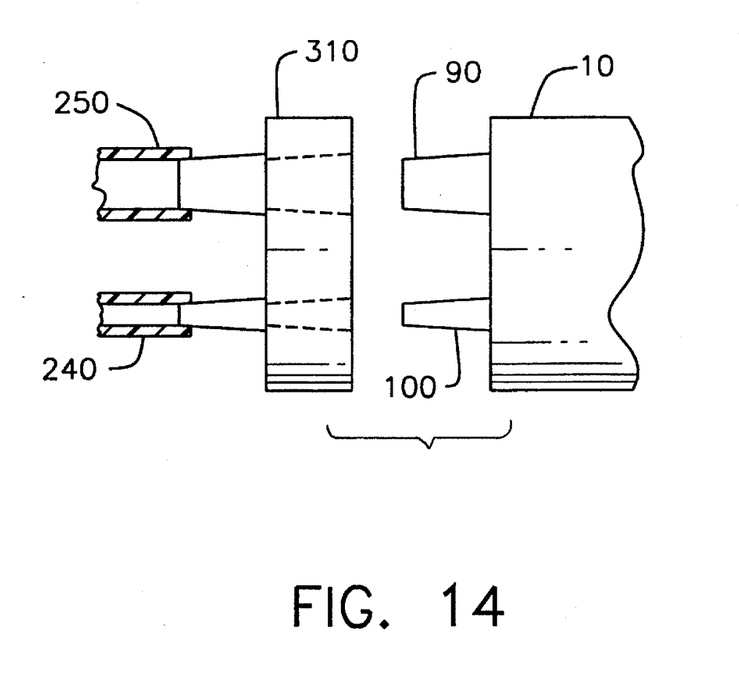
FIG. 14 is a side elevational view of an auxilliary device which can be used with the valve of the invention.

As shown in U.S. Pat. No. 4,995,387 of Walter J. Jinotti which is incorporated herein by reference and referring to FIG. 14, a rigid coupling member 310 is coupled to the output tubes of the valve and to the flexible tubes 240 and 250 which lead to the patient.

Figure 15:
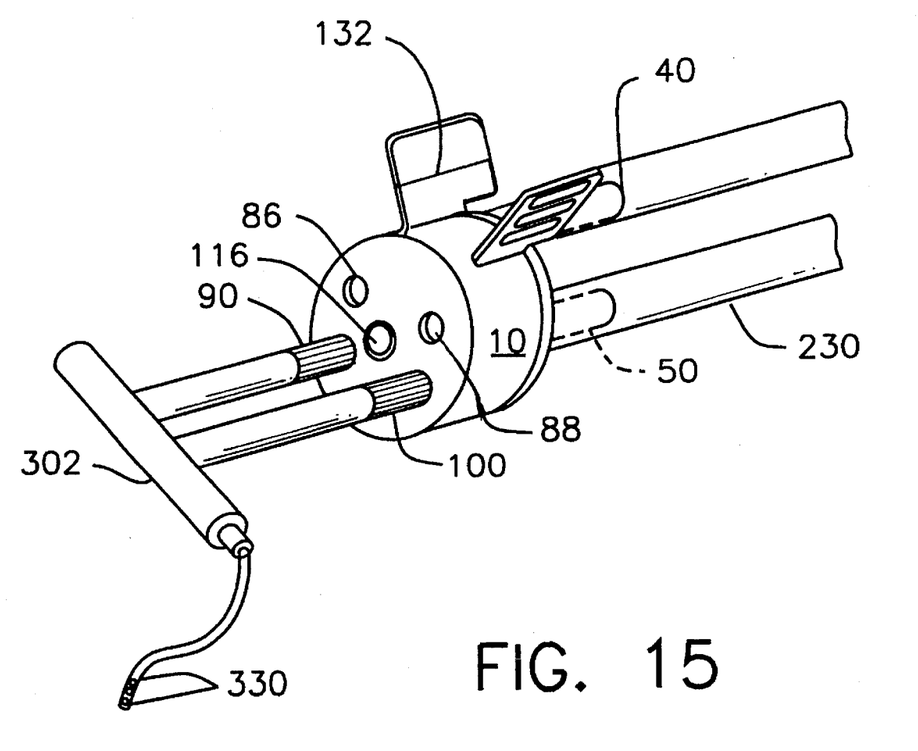
FIG. 15 is a perspective view of another device which can be used with the valve of the invention.

In addition, as shown in U.S. Pat. No. 5,255,672 of Walter J. Jinotti which is incorporated herein by reference and referring to FIG. 15, a manifold or coupling member 302 can be coupled to the output tubes 90 and 100 to provide a single feed tube 130 to the patient, a pediatric patient.

Other U.S. patents included herein by reference include U.S. Pat. Nos. 5,346,478; 5,140,983 and 5,088,486.

What is claimed is:

1. A valve for pulmonary treatment apparatus comprising a first valve portion, a second valve portion, first locking means forming a unitary piece with with said first valve portion, and second locking means forming a unitary piece with with said second valve portion, said first locking means tightly engaging said second locking means and exerting a pulling force which causes said first and second valve portions to be pulled toward each other and tightly locked together, thus locked together, said first and second valve portions are rotatable with respect to each other between a first orientation and a second orientation.

2. The valve defined in claim 1 and including a first finger tab on said first valve portion and a second finger tab on said second valve portion.

3. The valve defined in claim 1 and including venting means for venting suction and oxygen in said second valve portion.

4. The valve defined in claim 1 wherein said first locking means comprises a post having an end and said second locking means comprises a tube which receives said post and locks to said end of said post.

5. The valve defined in claim 1 and including a spring having a first end and a second end, the first end of said spring being secured to said first valve portion and the second end of said spring being secured to said second valve portion, said spring having a first position in which said first and second valve portions have said first orientation with respect to each other, said spring having a second position in which said first and second valve portions are rotated with respect to each other to said second orientation.

6. The valve defined in claim 1 and including an oxygen inlet tube coupled to said first valve portion and a suction inlet tube coupled to said first valve portion, and an oxygen outlet tube coupled to said second valve portion and a suction outlet tube coupled to said second valve portion, in said first orientation of said first and second valve portions with respect to each other, said first oxygen inlet tube is aligned with said oxygen outlet tube so that oxygen can flow through said valve to a patient and in said second orientation of said first and second valve portions with respect to each other said suction inlet tube is aligned with said output suction tube so that suction can be applied through said valve to a patient.

7. The valve defined in claim 6 and including blocking means on said first valve portion inside said valve positioned so that in one orientation of said first and second valve portions, said oxygen outlet tube is blocked and in the other orientation of said first and second valve portions, said suction outlet tube is blocked.

8. The valve defined in claim 1 wherein said first locking means comprises a post secured to said first valve portion and having an end remote from said first valve portion and said second locking means comprises a tube secured to said second valve portion which receives said post and locks to said end of said post.

9. The valve defined in claim 8 wherein said end of said post includes an annular indentation which engages a portion of said tube.

10. The valve defined in claim 1 wherein said first and second valve portions are coupled together so that they rotate with respect to each other, said valve including a spring disposed within said valve urging said first and second valve portions toward said first orientation.

11. The valve defined in claim 10 wherein said spring is a leaf spring.

12. The valve defined in claim 11 wherein said blocking means comprises two solid posts secured to said first portion of said valve inside said valve.

13. A valve for pulmonary treatment apparatus comprising a first valve portion including a body in the form of a plate having a flat bottom surface and a flat top surface, an input oxygen tube on said top surface and aligned with an opening in said top surface and an input suction tube on said top surface and aligned with an opening in said top surface, an inner suction tube and an inner oxygen tube on said bottom wall of said first valve portion, a first finger tab extending from said body of said first valve portion and accessible to an operator, a first locking member on said bottom surface of said plate of said first portion, said first locking member forming a unitary piece with said first portion, a second valve portion having a body in the form of a dish having a flat bottom wall and a surrounding wall, said bottom wall having a top surface and a bottom surface, an oxygen outlet tube and a suction outlet tube on said bottom wall of said body of said second valve portion, an opening in said bottom wall between said inner suction tube and said outlet suction tube, an opening in said bottom wall between said inner oxygen tube and said outlet oxygen tube, a second finger tab extending from said second portion of said valve, a second locking member forming a unitary piece with with said second portion of said valve, and said first locking member being aligned with said second locking member and secured thereto to couple said first and second portions of said valve together, said first and second locking members including means pulling said first and second portions of said valve toward each other to form a tight fit therebetween.

14. The valve defined in claim 13 and including a spring inside said valve and in said second valve portion and lying against said surrounding wall, said spring having end tabs which engage said first and second finger portions to hold them apart.

15. The apparatus defined in claim 13 and including a lead spring lying within said second valve portion and having a first end which engages said first finger tab and a second end which engages said second finger tab whereby said first and second finger tabs a are urged apart thereby.

16. The valve defined in claim 13 wherein said first locking means comprises a post having an end remote from said plate, said end having an annular notch adjacent to said end and a pair of tabs spaced from said notch, and said second locking means comprises a funnel like tube having a remote end into which said end of said first locking means is inserted and is engaged by said notch to hold said first and second locking means firmly together and to pull them toward each other.

17. The valve defined in claim 13 wherein said first locking member includes a first locking portion secured to the lower surface of said disk and being in the form of a truncated cone which tapers from a large diameter at said disk to a smaller diameter away from said disk, a second locking portion extending from said smaller diameter of said first portion and being in the form of a trucated cone having its smaller diameter at said first locking portion and its smaller diameter away from said first locking portion and a tip extending from said second locking portion and having two opposed laterally extending tabs, said second locking member extending upwardly from said top surface of said bottom wall of said second portion of said valve to an upper portion and including a tubular portion which extends downwardly from said upper portion to a lower end, the wall of said tubular portion being able to flex, a plurality of slots in said inner wall of said tubular portion, the lower end of said tubular portion engaging said slots and providing a pull on said first locking member to pull the two portions of said valve tightly together, said two tabs preventing said first locking member from being disconnected from said second locking member.

18. A valve for pulmonary treatment apparatus comprising a first valve portion having an outer surface and an inner surface, an oxygen supply tube and a suction supply tube extending from said outer surface of said first valve portion, a second valve portion having an outer surface and an inner surface, an oxygen output tube and a suction output tube extending from said outer surface of said second valve portion, means inside said valve between said first and second valve portions for coupling said oxygen input tube to said oxygen output tube and said suction input tube to said suction output tube, first locking means forming a unitary piece with with said first valve portion and extending from said inner surface thereof, second locking means forming a unitary piece with with said said second valve portion and extending from said inner surface thereof, said first locking means tightly engaging said second locking means and exerting a pulling force which causes said first and second valve portions to be pulled toward each other and tightly locked together, thus locked together, said first and second valve portions are rotatable with respect to each other between a first and a second orientation thereof.

19. A valve for pulmonary treatment apparatus comprising a first valve portion and a second valve portion tightly secured together and rotatable with respect to each and forming a generally fluid tight assembly, a first finger tab on said first valve portion and a second finger tab on said second valve portion, said first and second finger tabs being manipulated by an operator to rotate said first and second valve portions with respect to each other, said first valve portion having an inner surface and an outer surface, said second valve portion having an inner surface and an outer surface, said inner surface of said first valve portion and said inner surface of said second valve portion facing each other on the inside of said valve, a fluid supply tube and a suction supply tube extending from said outer surface of said first valve portion, a fluid output tube and a suction output tube extending from said outer surface of said second valve portion, means inside said valve for selectively and alternately coupling said fluid supply tube to said fluid output tube and said suction supply tube to said suction output tube, a first coupling tube extending from said inner surface of said first valve portion, a second coupling tube extending from said inner surface of said second valve portion toward and engaging said first coupling tube of said first valve portion, a spring inside said valve and having a first end and a second end, said first end of said spring engaging a portion of said first valve portion and said second end of said spring engaging a portion of said second valve portion, whereby with said finger tabs apart and said first and second valve portions in a first orientation with respect to each other, said spring is in a first state of tension and with said finger tabs squeezed together and said first and second valve portions are in a second orientation with respect to each other, said spring is under tension and tends to urge said finger tabs apart and said first and second valve portions to said first orientation, whereby in said first orientation of said first and second valve portions, one of said input tubes is coupled to one of said output tubes and in said second orientation, the other of said input tubes is coupled to the other of said output tubes so that in one of said orientations, oxygen is fed to a patient and in the other of said orientations, suction is fed to a patient, and means securely coupling together said first and second valve portions.

\* \* \* \* \*